United States Patent [19]
Beadle et al.

[11] Patent Number: 5,457,240
[45] Date of Patent: Oct. 10, 1995

[54] USE OF STRIPPER REACTOR REFLUX AS AN INITIATOR FOR PREFORMING REACTION OF COBALTOUS SALTS TO COBALT CARBONYLS

[75] Inventors: Stephen W. Beadle, Baton Rouge, La.; Claude A. Poulin, Randolph, N.J.

[73] Assignee: Exxon Chemical Patents, Inc., Wilmington, Del.

[21] Appl. No.: 356,035

[22] Filed: Dec. 14, 1994

Related U.S. Application Data

[63] Continuation of Ser. No. 178,697, Jan. 10, 1994, abandoned.

[51] Int. Cl.⁶ ............................. C07C 45/50; C07C 27/22
[52] U.S. Cl. ..................... 568/451; 502/26; 568/452; 568/492; 568/882; 568/883
[58] Field of Search ........................... 502/260; 568/451, 568/454, 492, 881, 882, 883, 452

[56] References Cited

U.S. PATENT DOCUMENTS

| | | | |
|---|---|---|---|
| 2,595,096 | 4/1952 | Parker et al. | 568/451 |
| 2,744,921 | 5/1956 | Mertzweiller et al. | 568/451 |
| 2,757,203 | 7/1956 | Hale | 568/451 |
| 2,757,204 | 7/1956 | Ratcliff | 568/451 |
| 2,779,794 | 1/1957 | Catteral | 568/451 |
| 2,779,796 | 1/1957 | Munger et al. | 568/451 |
| 2,816,933 | 12/1957 | Mertzweiller et al. | 568/451 |
| 2,905,716 | 9/1959 | Buchner et al. | 568/451 |
| 3,092,670 | 6/1963 | Gwyn et al. | 568/451 |
| 3,196,171 | 7/1965 | Guneer et al. | 568/451 |
| 3,520,937 | 7/1970 | Moell et al. | 568/451 |
| 3,725,534 | 4/1973 | Reisch | 423/417 |
| 3,868,422 | 2/1975 | Hart et al. | 568/451 |
| 3,941,848 | 3/1976 | Hummer et al. | 568/451 |
| 4,625,067 | 11/1986 | Hanin | 568/451 |
| 5,091,599 | 2/1992 | DeMunck et al. | 568/882 |
| 5,235,112 | 8/1993 | Nadler et al. | 568/451 |
| 5,237,105 | 8/1993 | Summerlin | 568/451 |
| 5,321,168 | 6/1994 | Roussel et al. | 568/882 |

*Primary Examiner*—Werren B. Lone
*Attorney, Agent, or Firm*—Richard D. Jordan

[57] ABSTRACT

A method for starting a preformer reactor disposed within a hydroformylation system which comprises an oxo reactor, a stripper reactor and a preformer reactor, wherein the bottoms from the stripper reactor comprise at least a water soluble cobaltous salt and wherein the overhead from the stripper reactor comprises entrained volatile cobalt compounds, wherein at least a portion of the entrained volatile cobalt compounds from the stripper reactor are recycled to the preformer reactor to act an initiator in the conversion of the cobaltous salt to cobalt carbonyl.

20 Claims, 3 Drawing Sheets

USE OF STRIPPER REACTOR REFLUX AS AN INITIATOR FOR PREFORMING REACTION OF COBALTOUS SALTS TO COBALT CARBONYLS

This is a continuation of application Ser. No. 08/178,697, filed Jan. 10, 1994, now abandoned.

The present invention relates generally to a method for hydroformylating an olefin feedstock via reaction with carbon monoxide and hydrogen in the presence of a carbonylation catalyst. In particular, it relates to the recycling of a portion of the reflux comprising hydridocobalt tetracarbonyl from the stripper reactor to the preformer reactor such that the reflux acts as an initiator in the conversion of cobaltous salts to cobalt carbonyls.

BACKGROUND OF THE INVENTION

Hydroformylation reactions involve the preparation of oxygenated organic compounds by the reaction of carbon monoxide and hydrogen (a.k.a., syn or synthesis gas) with carbon compounds containing olefinic unsaturation. The reaction is performed in the presence of a carbonylation catalyst and results in the formation of a compound, for example an aldehyde, which has one more carbon atom in its molecular structure than the starting olefinic feedstock. By way of example, higher alcohols may be produced in the so-called "oxo" process by hydroformylation of commercial $C_6$–$C_{12}$ olefin fractions to an aldehyde-containing oxonation product, which on hydrogenation yields respective $C_7$–$C_{13}$ saturated alcohols. The crude product of the hydroformylation reaction will contain catalyst, aldehydes, alcohols, unreacted feed, syn gas and by-products.

Before further processing of the crude product is possible, it is necessary to remove the catalyst therefrom. One conventional method of removing cobalt values from such a crude product is set forth in U.S. Pat. No. 4,625,067 (Hanin), which issued on Nov. 25, 1986. The process disclosed in Hanin involves the contacting of the crude product with a stream of stripping gas to entrain volatile cobalt compounds, characterized in that the contacting is performed in the presence of water and aqueous acid to dissolve those cobalt values not entrained in the gas under the conditions of temperature and pressure employed for the contacting, and the aqueous phase is subsequently separated from the organic hydroformylation reaction product.

The Hanin patent has the disadvantage that when lower carbon number olefins (e.g., $C_7$ and below) are used as the feedstock, unreacted compounds such as olefins and/or paraffins are stripped out together with the volatile cobalt compounds. These olefins and/or paraffins are then absorbed into the olefinic feedstock and recycled to the oxo reactor. This occurs because lower carbon number feedstocks such as heptene have roughly the same volatility as the cobalt specie, thereby causing it to be entrained together with the volatile cobalt and taken out overhead. Light hydrocarbons which are absorbed into the olefinic feedstock rapidly build up within the cobalt recovery system causing an undesirable decrease in net olefin feed rate.

U.S. Pat. No. 5,237,105 (Summerlin), which issued on Aug. 17, 1993, discloses a method of recovering cobalt values which does not cause the build up of unreacted light hydrocarbons within the system, thereby avoiding a decrease in the olefin feed rate. This is accomplished by providing a demetalling step prior to the stripping step which produces a substantially cobalt-free organic hydroformylation reaction product and water soluble cobaltous salt aqueous product. The organic hydroformylation reaction product is diverted for further downstream treatment, while the water soluble cobaltous salt aqueous product is concentrated, converted to cobalt carbonyl and stripped of volatile cobalts which are substantially free of any light hydrocarbons using a recirculating alcohol.

For alcohol grades containing eight or more carbon numbers the catalyst cycles of Hanin and Summerlin are similar. The common feature being a stripper reactor which recovers greater than 70% of the cobalt contained in the oxonation stream overhead where it is absorbed from the gas stream by the entering olefin feed stream. In order to maintain cobalt balance the additional 30% of the cobalt must be produced by taking the aqueous cobalt formate stream from the stripper reactor bottoms converting it to a cobalt carbonyl via a preformer reactor. As the alcohol content decreases and carbon number increases the preforming efficiency of the oxonation product decreases.

The Hanin patent discloses two phase non-catalyzed preforming. In order to decrease the volume of the preformer and to facilitate grade switching the Summerlin patent uses a catalyzed system.

The Summerlin patent also discloses an alternative mode of operation (i.e., the demet mode) which is used for lower carbon number grades. In the demet mode, the oxonation product is decobalted by an air oxidation of the cobalt carbonyls to water soluble cobalt formate. The decobalted oxo product is water washed and sent to the hydrogenation section. The cobalt formate stream is concentrated in an evaporator and mixed with hexyl alcohol before being fed to a preformer reactor. The preformer product is fed to a stripper reactor where the cobalt carbonyls are stripper overhead as in the Cobalt Flash operating mode. The hexyl alcohol bottoms are recycled to the preformer, and the cobalt formate is sent to the demetalling section for trace carbonyl cleanup. This mode of operation requires that 100% of the cobalt carbonyl be generated in the preformer versus 30% in the Cobalt Flash mode. This is feasible since the hexyl alcohol stream is a much more efficient preforming organic than oxonation product.

In both the Hanin and Summerlin patents, the reflux from the stripper reactor is passed to an absorber where it is contacted with a feed olefin for recycling either to the oxo reactor or to the stripper reactor. This reflux consists mainly of water and cobalt carbonyls, containing from 800 to 2600 ppm cobalt. The present inventors have recognized that certain advantages can be gained by diverting at least a portion of the stripper reactor reflux to the preformer reactor instead of the absorber. Stripper reactor reflux which is diverted to the preformer reactor can be used as a preforming reaction initiator. Since the preforming reaction is autocatalytic, the use of stripper reactor reflux as a preformer initiator will speed up the reaction which results in a smaller reactor volume and reduces or eliminates the need for a heterogeneous preforming catalyst.

The present invention offers optimization opportunities for both the Cobalt Flash mode which is disclosed in both the Hanin and Summerlin patents and the demet mode which is disclosed solely in the Summerlin patent.

In accordance with the Cobalt Flash mode as disclosed in the Hanin patent, a two phase non-catalyzed preformer is used. The preformer has an inherent inhibition time when oxo product is used for the preforming organic. The present invention provides for the recycling of the stripper reactor reflux introduces $HCo(CO)_4$ to the preformer reactor, wherein the $HCo(CO)_4$ acts as a reaction initiator so as to greatly reduce or eliminate inhibition time. This will in turn permit the use of a smaller preformer reactor and greatly simplify and speed up olefin grade switching when no other source of cobalt carbonyl is present. This would require a holding drum, etc. for the stripper reactor reflux.

In a catalyzed preformer reactor as disclosed in the Cobalt Flash mode of the Summerlin patent, the incentives are to reduce catalyst costs or to compensate for deactivated catalyst. The recycling of the reflux from the stripper reactor to the preformer has been found to be useful in this mode since it substantially reduces or eliminates the need for a preformer catalyst.

When light grades are hydroformylated under Summerlin's demet mode of operation, hexyl alcohol is used and has been found to be very efficient. For a deactivated catalyst system, however, the recycling of the stripper reactor reflux to the preformer actually improves the operation and perhaps even extends the catalyst's service life.

The present invention also provides many additional advantages which shall become apparent as described below.

SUMMARY OF THE INVENTION

A method for initiating the reaction which takes place in a preformer of a hydroformylation process operating under either a Cobalt Flash mode or a demet mode. The preformer reaction is initiated by recycling at least a portion of the reflux (i.e., a stream containing water and cobalt carbonyls (e.g., $HCo(CO)_4$)) generated overhead from a stripper reactor of the hydroformylation system to the preformer reactor. This reflux is particularly useful in initiating the reaction of cobalt formate and synthesis gas (e.g., carbon monoxide and hydrogen) to form hydridocobalt tetracarbonyl ($HCo(CO)_4$).

Other and further objects, advantages and features of the present invention will be understood by reference to the following specification in conjunction with the annexed drawings, wherein like parts have been given like numbers.

DESCRIPTION OF THE PREFERRED EMBODIMENTS

Figure 1:
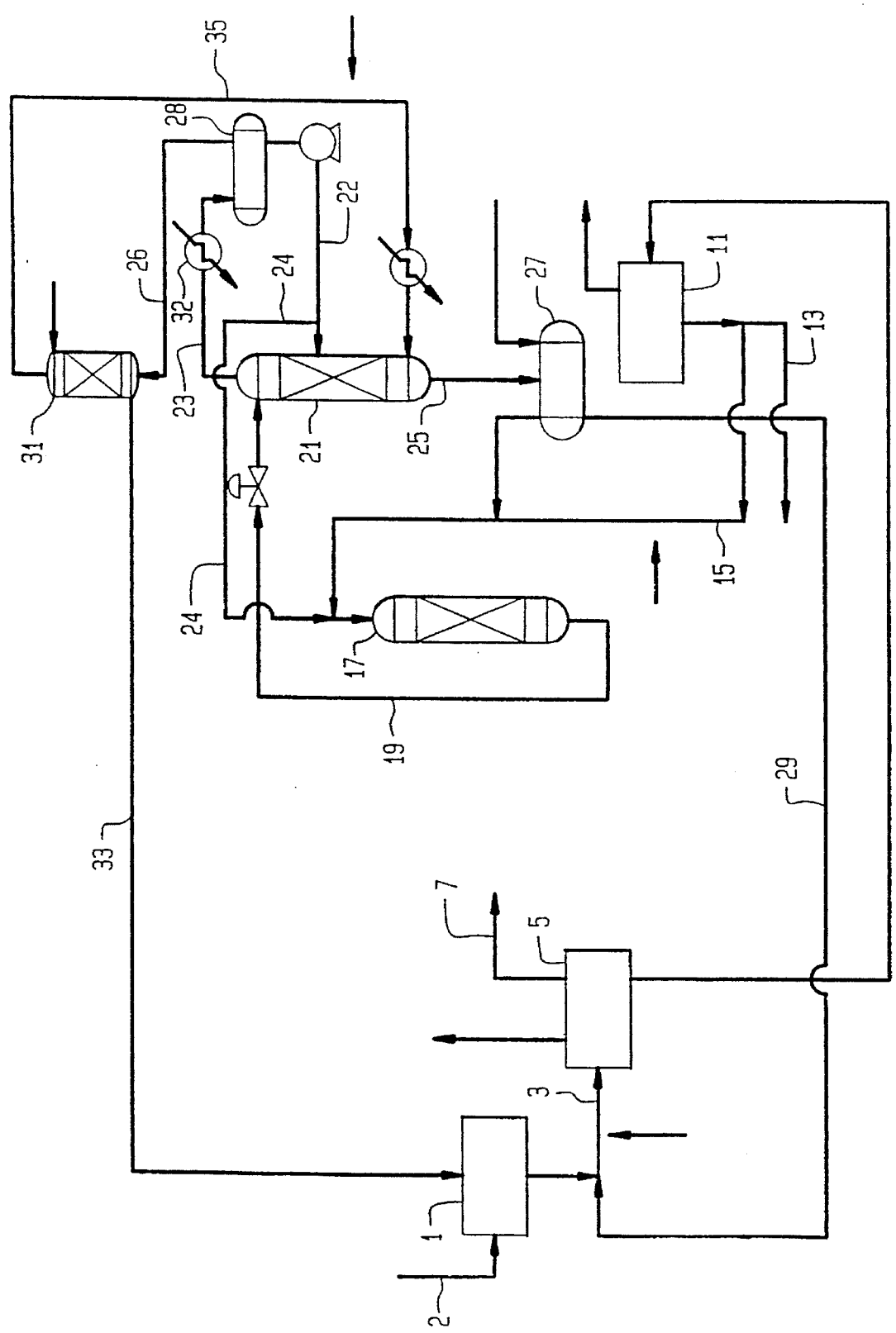
FIG. 1 is a flow diagram of a hydroformylation reaction system embodying the process of the present invention which is operating under the demet mode.

U.S. Pat. Nos. 4,625,067 (Hanin) and 5,237,105 (Summerlin), which are incorporated herein by reference, disclose various methods of hydroformylating unsaturated olefin feedstocks wherein the oxo catalyst is removed from the crude reaction product by means of a stripper reactor. After contacting the crude product with a stripping gas, the cobalt-containing aqueous phase is separated from the treated cobalt-free organic product and recycled via a reflux unit and absorber to the hydroformylation reaction to ensure that catalyst concentration in the reaction zone is maintained, since under oxonation conditions the cobalt in the concentrate converts to the active catalytic species useful in hydroformylation.

In some systems, such as the present invention, it is preferred not to recycle the aqueous cobalt concentrate to the hydroformylation reactor. For example, where the reactor is susceptible to corrosion such recycle would not be desirable. One option is to deliver the concentrate to a cobalt preformer unit. The aqueous concentrate, especially when not based on an inorganic acid, is introduced into the cobalt preformer, and the resulting mixture is injected into the crude oxo product downstream of the oxo reactor but upstream of the stripper unit, or directly into the stripper unit. Here the stripping gas carries off the volatile cobalt carbonyls present (including those newly introduced to the system from the cobalt preformer) and, via extraction into the olefin feed, into the oxo reactor. By such an embodiment only minimal quantities of fresh cobalt need be introduced into the cobalt preformer, as make-up for an otherwise closed system.

However, because the two phase non-catalyzed preformer has a relatively slow start-up time and because of the high cost of palladium catalyst, it has been discovered by the present inventors that by recycling at least a portion of the reflux from the stripper reactor overhead stream to the preformer reactor, the cobalt carbonyl (e.g., hydridocobalt tetracarbonyl) present in the reflux can act as a reaction initiator, thereby increasing the speed of reaction, reducing the reactor volume, and reduce or eliminate the need for the palladium catalyst. When the stripper reactor reflux is used as a reaction initiator in the preformer reactor it is present in an amount between about 200 to about 1,500 ppm cobalt per weight of total preformer feed.

In accordance with the preferred embodiment of the present invention (i.e., the application of an acid-air cobalt demetalling step upstream of the stripping step of a Cobalt Flash hydroformylation catalyst recovery process) air, water, and a organic acid (e.g., formic acid) are mixed with the crude product from an oxo reactor in the acid-air demetalling step described above and allowed to settle. The water stream containing a water soluble cobaltous salt is thereafter separated from the now cobalt-free organic hydroformylation reaction product which is sent directly to hydrogenation thus bypassing the conventional stripping step. The water soluble cobaltous salt is thereafter mixed with the water stream bottoms from the stripper reactor which also contains a cobaltous salt product and these combined streams are fed to an evaporator. The water stream bottoms from the stripper reactor are also sent through the acid-air demetalling step to convert any trace carbonyls to cobalt formate. The evaporator concentrates the cobaltous salt and generates an overhead stream of cobalt-free water and organic acid which are recycled as wash water and for use in the acid-air demetalling step. The concentrated cobaltous salt stream is mixed with an alcohol stream and fed to a preforming reactor where the cobaltous salt is converted to cobalt carbonyls and then fed to the stripper reactor where the cobalt is stripped overhead using synthesis gas and then absorbed in the feed olefin. The alcohol stream is preferably taken from the bottoms stream of the stripper reactor and recycled back to the preformer reactor.

Accordingly, substantially all of the organic hydroformylation product is separated from the cobaltous salt product wherein the organic hydroformylation product bypasses the stripper reactor and is sent directly to a hydrogenation or distillation step. As such, the lighter hydrocarbons do not enter the stripper reactor and therefore cannot be entrained together with volatile cobalt. Since the lighter hydrocarbons are not entrained within the volatile cobalt they cannot be absorbed into the olefin feedstock and thus neither build-up within the catalyst recovery cycle nor do they effect the net olefin feed rate.

An alternative embodiment of this invention includes the application of an acid-air cobalt demetalling step downstream of the stripping step of a Cobalt Flash hydroformylation catalyst recovery process and the recycling of the cobalt carbonyl reflux from the stripper reactor to the preformer reactor. This embodiment is particularly useful in decobalting heavier hydrocarbons (i.e., heavier than heptene). In accordance with this embodiment, crude oxonation product bypasses the acid-air demetalling step and, after addition of a organic acid and water, goes directly to the stripper reactor where approximately 70% of the cobalt is stripped overhead as cobalt carbonyl using synthesis gas. The cobalt taken overhead is subsequently either recycled to the preformer reactor as a reaction initiator or absorbed into the feed olefin. The vast majority of the cobalt taken overhead is sent to the absorber. The remaining cobalt leaves the stripper reactor as a cobaltous salt via the bottoms stream. This cobaltous salt along with recycled wash water is then be routed to the acid-air demetalling step to remove any trace levels of cobalt carbonyls. The demetalled water stream is then diverted to the evaporator and concentrated. This concentrated cobaltous salt is thereafter mixed with a portion of the cobalt-free organic hydroformylation reaction product from the stripper bottoms stream, or an alcohol product, or recycled hydrogenation product and fed to the preforming reactor. The preformer product is mixed with the oxonation product and fed to the stripper reactor.

The stripping gas which is preferably used in accordance with this invention is synthesis gas (i.e., carbon monoxide and hydrogen mixture). The particular proportions of the two components in the synthesis gas being adjusted to suit the reaction system.

It is preferred that the volume ratio of stripping gas to crude product at the applied conditions be from 20:1 to 250:1, more preferably 50:1 to 125:1. Of course a higher ratio may be used, with good effect, but higher ratios may be detrimental to the economic basis of the process. The limiting lower value of the ratio, it will be appreciated, will be reached when there is insufficient stripping gas flow to achieve the desired degree of volatile cobalt removal. Similarly, any flow rate of stripping gas may be used, sufficient to give the desired entrainment of volatile cobalt. The liquid (i.e., organic plus aqueous) phase is preferably well dispersed to give good contact between the liquids. It is preferred, too, that the stripper reactor include inert solid surfaces or trays to facilitate contact between the liquid and gas phases.

The stripping reactor preferably operates at relatively low pressures, i.e., pressures lower than the decomposition pressure of the cobalt compounds present in the crude hydroformylation reaction product at the temperature conditions employed. More preferably the pressure is below 20.26 bar, most preferably below 10.13 bar, especially for example a low pressure below 7.091 bar such as from 1.013 to 5.065 bar. The temperature employed generally relates to the pressure and is preferably less than or no more than 100° C. or 90° C., more preferably from 60°–100° C., especially 60° to 80°, 85° or 90° C. The temperature in the stripper bottoms is preferably between about 88°–93° C.

In accordance with either the Cobalt Flash or demet mode of operation, the demetalling step is preferably followed by a preformer reactor. The concentrated cobaltous salt is preferably introduced into the cobalt preformer, and the resulting mixture is injected, under the Cobalt Flash mode, into the crude oxo product downstream of the oxo reactor but upstream of the stripper reactor, or directly into the stripper reactor. Here the stripping gas carries off the volatile cobalt carbonyls (including those newly introduced to the system from the cobalt preformer) and, via absorption into the olefin feed, into the oxo reactor. By such an embodiment only minimal quantities of fresh cobalt need be introduced into the oxo reactor, as make up for an otherwise closed system.

The preformer reaction resulting in the formation of cobalt carbonyl compounds is promoted with a noble metal catalyst, in particular a catalyst selected from the metals of Group IB and VIII of the Periodic Table. Representative examples of useful catalyst material include gold, platinum and palladium. Palladium is the preferred catalyst metal. Preferably, the active catalyst materials are embedded on a solid support such as carbon, coke or alumina. Typically, when a supported catalyst system is used, the active catalyst metal makes up approximately 0.1 to 5.0 weight percent, preferably 0.2 to 2.0 weight percent of the total supported catalyst structure.

However, depending upon the cobalt concentration in the reflux stream of the stripper reactor which is recycled to the preformer reactor, the need for a preformer catalyst may be reduced or eliminated. That is, the cobalt carbonyl which is entrained in the stripper reactor reflux may provide sufficient catalytic activity for the completion of the reaction of cobalt formate to hydridocobalt tetracarbonyl at a temperature of between about 100° and about 175° C. and at a pressure of between about 103 and about 310 bar.

The present inventors believe that the volatile cobalt carbonyl refluxed from the stripper reactor acts as a reaction initiator or spike, wherein the reaction of cobalt formate and syn gas occurs under the appropriate temperature and pressure without the need for additional preformer catalyst. Addition of between about 200 to about 1,500 ppm cobalt carbonyl to the preformer reactor as an initiator is sufficient to obviate the need for additional preformer catalyst.

The invention may be better understood by reference to the drawings, wherein FIG. 1 illustrates a method for removing cobalt values wherein an acid-air cobalt demetalling step is disposed upstream of the stripping step in a Cobalt Flash process and wherein the reflux from the stripper reactor is recycled to the preformer reactor.

FIG. 1 generally depicts a method for removing cobalt values from the crude product of a cobalt-catalyzed hydroformylation reaction formed from an olefinic feedstock having a carbon number in the range $C_4$–$C_{14}$, preferably $C_5$–$C_7$. The crude product typically contains cobalt compounds in addition to an organic hydroformylation reaction product.

An olefin feedstock and syn gas are introduced into oxo reactor 1 via conduits 33 and 2, respectively, wherein hydroformylation is conducted under conventional conditions to yield a crude hydroformylation product containing aldehydes, alcohols, by-products and cobalt catalyst compounds. This crude product is carried via conduit 3 where it is contacted with a stream of oxygen-containing gas, an organic acid and water, thereby producing a substantially cobalt-free organic hydroformylation reaction product and a water soluble cobaltous salt aqueous product, to settling drum or demetalling drum 5. In demetalling drum 5 the substantially cobalt-free crude product is separated from the water soluble cobaltous salt aqueous product. The substantially cobalt-free organic hydroformylation reaction product is diverted overhead via conduit 7 for further downstream treatment such as distillation or hydrogenation. The water soluble cobaltous salt aqueous product is carried via conduit 9 to evaporator 11 which concentrates the water soluble cobaltous salt, thereby producing a concentrated aqueous solution of cobaltous salt and a substantially cobalt-free water containing the organic acid, whereby the concentrated aqueous solution of cobaltous salt is separated from the substantially cobalt-free water containing the organic acid. The substantially cobalt-free water from evaporator 11 is recycled via conduit 13 to oxo reactor 1. Whereas the concentrated aqueous solution of cobaltous salt is contacted with an alcohol stream and synthesis gas within conduit 15 before this mixture is passed to preformer reactor 17. In preformer reactor 17 the concentrated aqueous solution of cobaltous salt is converted to a cobalt carbonyl under catalytic conditions. The cobalt carbonyl from preformer reactor 17 is carried via conduit 19 to stripper reactor 21 where it is contacted with a stream of stripping gas at a temperature of not greater than 100° C. and at a pressure below 10.13 bar, the pressure being lower than the decomposition pressure of the cobalt compounds at the contacting temperature, to entrain volatile cobalt compounds in the stripping gas and to generate as bottoms alcohol products and dissolved cobaltous salts; whereby the entrained volatile cobalt compounds are taken out overhead via conduit 23 and the alcohol products and dissolved cobaltous salts are taken out as bottoms via conduit 25. The alcohol products are separated from the dissolved cobaltous salts in settling drum 27. The dissolved cobaltous salts are typically in an aqueous phase, e.g., an aqueous salt product, which can be readily separated from the organic phase, i.e., the alcohol products, by gravity settling. The alcohol products from settling drum 27 are preferably recycled to conduit 15 for mixing with the cobaltous salt upstream of preformer reactor 17. The cobaltous salt from settling drum 27 is preferably recycled via conduit 29 to conduit 3 for further demetalling. Finally, the volatile cobalt from conduit 23 are condensed via condenser 32 at a temperature in the range between about 130°–160° C. and then passed on to reflux unit 28 wherein gaseous $HCo(CO)_4$ is taken overhead via conduit 26 to absorber 31 and a reflux liquid product comprising water, organics and dissolved cobalt carbonyls is taken as bottoms. The reflux liquid product is either recycled via conduit 22 to stripper reactor 21 or sent via conduit 24 to preformer reactor 17 where it acts as a reactor initiator. The volatile cobalt which is introduced into absorber 31 contacts with olefinic feedstock, whereby the volatile cobalt is absorbed into the olefinic feedstock and recycled to oxo reactor 1 via conduit 33. The essentially cobalt-free gas stream from absorber 31 is returned to stripper reactor 21 via conduit 35. Optionally, synthesis gas make-up may also be fed into stripper reactor 21 via reflux conduit 35.

It is preferable that the oxygen-containing gas introduced into the system at conduit 3 be at least one selected from the group consisting of: air, air with nitrogen, carbon dioxide, and mixtures of inert gases with oxygen having an oxygen content in the range of about 2 to about 10%. The amount of oxygen-containing gas used in this catalyst removal process is a function of the cobalt contained in the crude oxo product. For example, if the oxygen-containing gas is a mixture of air and nitrogen, then the amount of air required to convert cobalt carbonyl to $Co^{+2}$ is approximately 130% of theoretical amount, i.e., 1.77 grams of air/gram of cobalt. Nitrogen can be used to dilute the mixture to about 4 volume % of $O_2$, i.e., 4.11 grams of $N_2$/gram of air. Thus, the air and nitrogen is added to the crude oxo product in an amount of approximately 8.81 grams of gas mixture/gram of cobalt. Since the cobalt concentration in commercial crude oxo products is preferably in the range from about 0.05 to about 0.50 weight %, the oxygen-containing gas is typically added to the crude oxo product in an amount between about 0.45 to about 4.50 weight %. The oxygen-containing gas is then used in an oxygen-containing gas to crude oxo product weight ratio of from about 0.0045:1 to 0.45:1.

The organic acid supplied to conduit 3 for use in the acid-air cobalt demetalling step is typically selected from the group consisting of: formic acid, acetic acid, propionic acid, and other acids having a boiling point approximately the same as water such that appreciable values of acid can be recovered in evaporator 27 for recycling to conduit 3 via conduit 29. It is most preferable that the organic acid be formic acid such that the resultant water soluble cobaltous salt is cobalt formate. The amount of organic acid which is added to the crude oxo product is a function of the amount of cobalt contained within the crude oxo product. Cobalt Flash processes are designed to used 140% of theoretical organic acid to convert cobalt carbonyl to cobalt formate. For example, formic acid may be added to the crude oxo product in an amount of about 2.18 grams of formic acid/gram of cobalt. Thus, if the cobalt concentration in the crude oxo product is in the range between about 0.05 to about 0.50 weight %, then the formic acid is preferably added to the crude oxo product in an amount between about 0.00109 to about 0.0109 grams of formic acid/gram of crude oxo product.

It is preferred that the concentration of the water soluble cobaltous salt aqueous product take place in either a flash unit or evaporator 11 by means of distillation or membrane separation.

Although it is preferable to convert the concentrated aqueous solution of cobaltous salt to a cobalt carbonyl in the presence of a noble metal catalyst disposed within preformer reactor 17, it is optional to convert by contacting of phases at a pressure in the range between about 103 bar (i.e., 1500 psig) to about 310 bar (i.e., 4500 psig) and a temperature in the range between about 100° C. to about 175° C.

It is also optional to subject the substantially cobalt-free organic hydroformylation reaction product diverted from demetalling drum 5 to a water wash treatment in order to remove residual cobalt values remaining therein prior to further downstream treatment such as distillation or hydrogenation. The wash water from this optional treatment can be recycled to conduit 3 to aid in demetalling of the crude oxo product. The water introduced in the acid-air demetalling step via conduit 3 is used in a water to crude product weight ratio of from 0.05:1 to 0.5:1. This ratio is based upon the assumption that 1 wt % cobalt concentration (as cobalt, not cobalt formate) in water is desirable.

Figure 2:
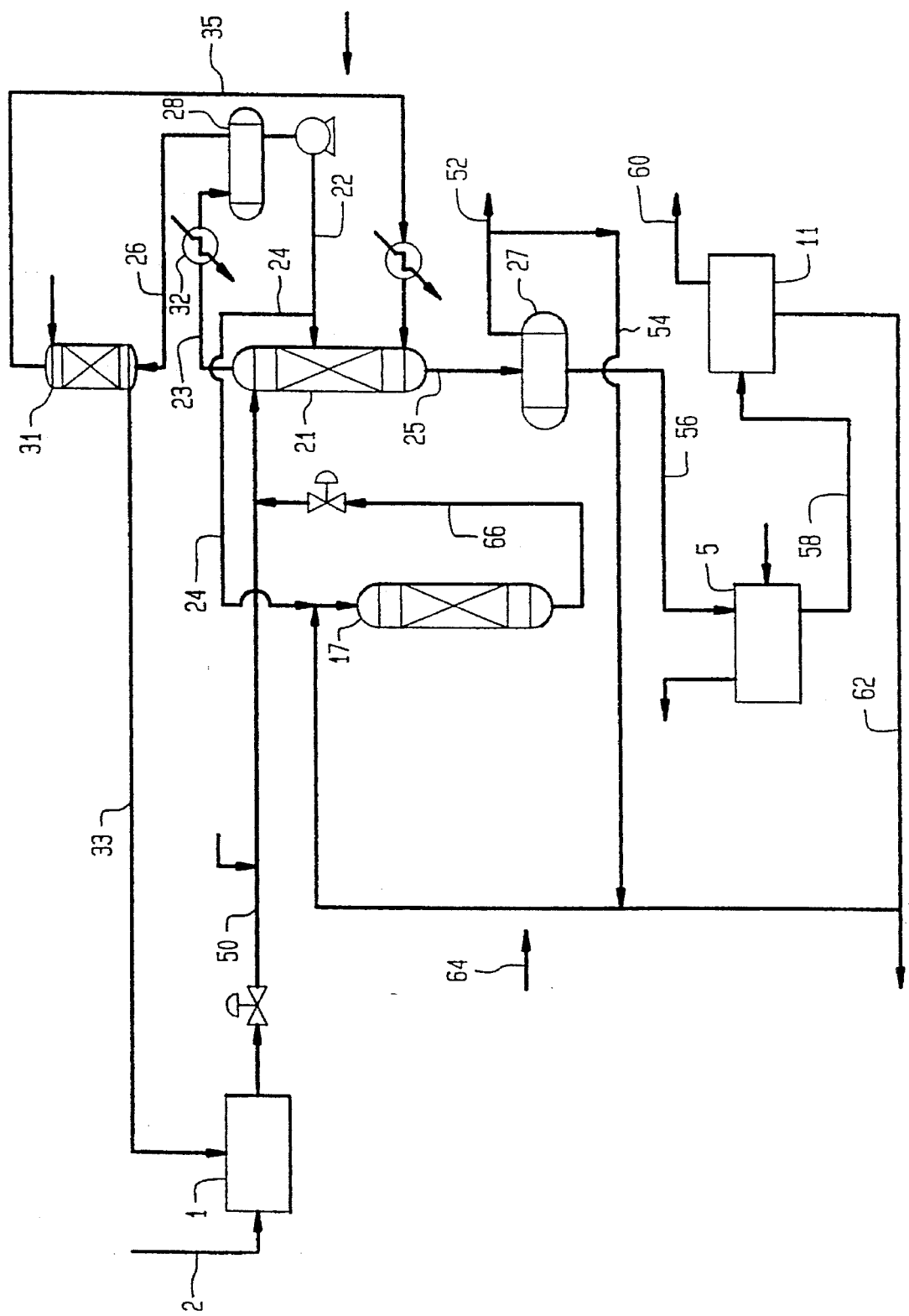
FIG. 2 is a flow diagram of a hydroformylation reaction system embodying another embodiment of the process of the present invention which is operating under the Cobalt Flash mode.

FIG. 2 depicts a method for removing cobalt values from the crude product of a cobalt-catalyzed hydroformylation reaction formed from an olefinic feedstock having a carbon number in the range of $C_7$–$C_{14}$, wherein an acid-air cobalt demetalling step is disposed downstream of the stripping step in a Cobalt Flash process and wherein a portion of the reflux from the stripper reactor is recycled to the preformer reactor.

An olefin feedstock and syn gas are introduced into oxo reactor 1 via conduits 33 and 2, respectively, wherein hydroformylation is conducted under conventional conditions to yield a crude hydroformylation product containing aldehydes, alcohols, by-products and cobalt catalyst compounds. This crude product is carried via conduit 50 where it is contacted with water and an organic acid, such as formic acid. The treated crude product is thereafter contacted with a stream of stripping gas in stripper reactor 21. The stripping typically occurs at a temperature of not greater than 100° C. and at a pressure below 10.13 bar, the pressure being lower than the decomposition pressure of the cobalt compounds at the contacting temperature, to entrain volatile cobalt compounds in the stripping gas, whereby the entrained volatile cobalt compounds are taken out overhead via conduit 23 and organic hydroformylation reaction products containing water soluble cobaltous salts dissolved therein are taken out as bottoms via conduit 25. The water soluble cobaltous salt is then separated from the organic hydroformylation reaction products by means of settling drum 27. The organic hydroformylation reaction product is then carried via conduit 52 for further downstream treatment such as distillation or hydrogenation. Optionally, a portion of the organic hydroformylation product may be diverted from conduit 52 via conduit 54 and recycled to the preformer reactor 17. The water soluble cobaltous salt is carried via conduit 56 to settling drum or demetalling drum 5 where it is contacted with a stream of oxygen-containing gas, an organic acid and water thereby producing a water soluble cobaltous salt aqueous product. Thereafter, the water soluble cobaltous salt aqueous product is carried via conduit 58 to evaporator 11 which forms a concentrated aqueous solution of cobaltous salt and a substantially cobalt-free water containing some organic acid. The concentrated aqueous solution of cobaltous salt is then separated from the substantially cobalt-free water containing the organic acid, whereby the substantially cobalt-free water containing the organic acid is recycled via conduit 60 to stripper reactor 21, diverted to the optional water wash treatment step, or diverted to hydrogenation. The concentrated aqueous solution of cobaltous salt is carried via conduit 62 either to preformer reactor 17 or recycled to oxo reactor 1. However, prior to being fed to preformer reactor 17, the concentrated cobaltous salt is contacted with an alcohol stream, a cobalt-free organic hydroformylation reaction product, or a hydrogenation product delivered via conduit 54 and syn gas which is delivered via conduit 64. This mixture is then passed on to preformer reactor 17 where the concentrated aqueous solution of cobaltous salt is converted to a cobalt carbonyl. The cobalt carbonyl is then carried via conduits 66 and 50 to stripper reactor 21. Finally, the volatile cobalt from conduit 23 are condensed via condenser 32 at a temperature in the range between about 130°–160° C. and then passed on to reflux unit 28 wherein $HCo(CO)_4$ is taken overhead via conduit 26 to absorber 31 and a reflux liquid product comprising water, organics and dissolved cobalt carbonyls is taken as bottoms. The reflux liquid product is either recycled via conduit 22 to stripper reactor 21 or sent via conduit 24 to preformer reactor 17 where it acts as a reactor initiator. The volatile cobalt which is introduced into absorber 31 contacts with olefinic feedstock, whereby the volatile cobalt is absorbed into the olefinic feedstock and recycled to oxo reactor 1 via conduit 33. The essentially cobalt-free gas stream from absorber 31 is returned to stripper reactor 21 via conduit 35.

Figure 3:
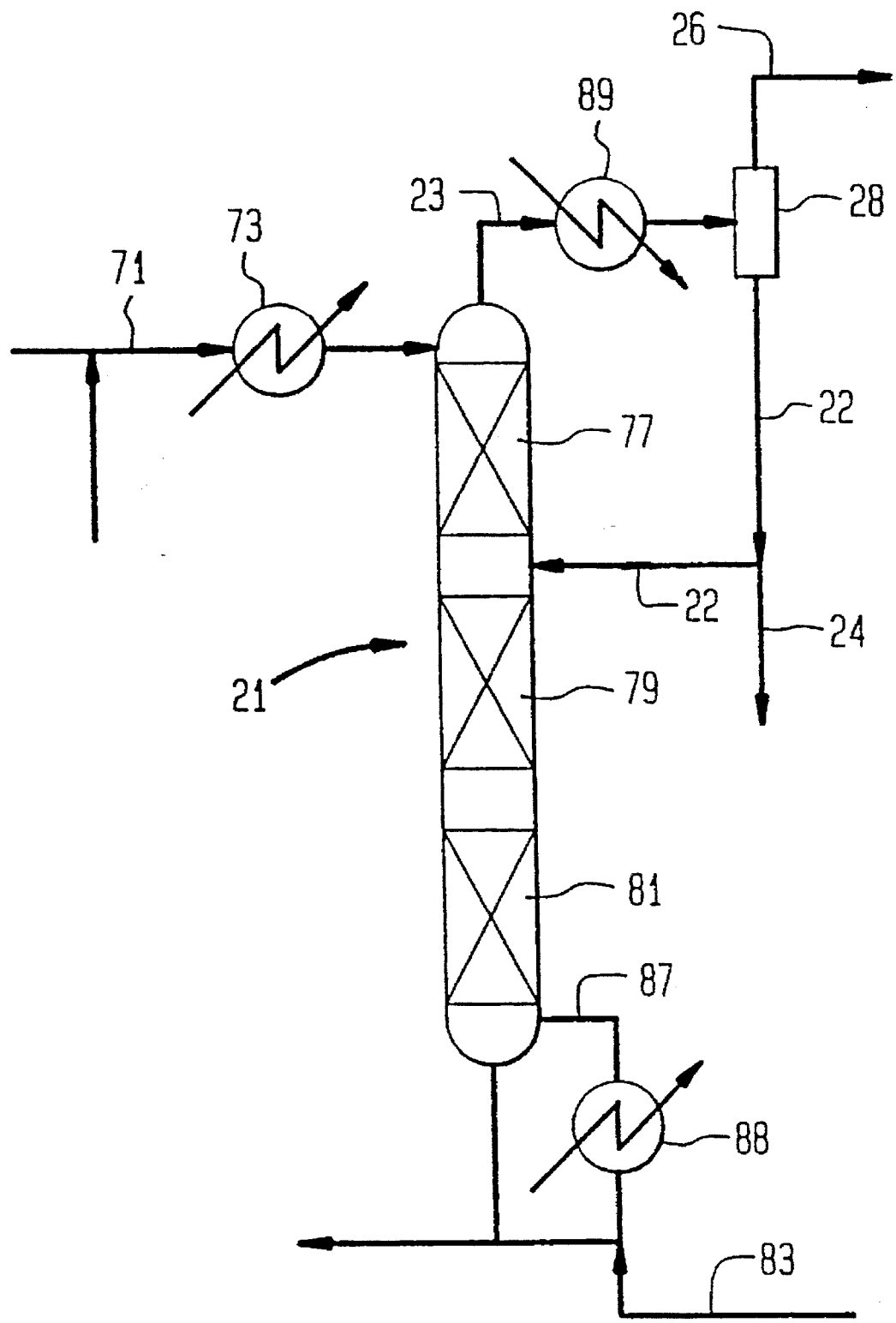
FIG. 3 is a schematic diagram of the preferred stripper reactor in accordance with the present invention.

A particularly desirable configuration of the stripper reactor is set forth in FIG. 3 and U.S. Pat. No. 5,235,112, which is incorporated herein by reference. In accordance with FIG. 3, crude oxo product containing cobalt is mixed with water and an organic acid, e.g., formic acid, and the resulting two-phase mixture is sent via conduit 71 and heat exchanger 73 to the top of stripper reactor 21. Stripper reactor 21 having an upper stripper section 77, an intermediate stripper section 79 and a lower stripper section 81. Preheated stripping gas, e.g., syn gas, feed via conduit 83 to the bottom of stripper reactor 21 such that it flows up through reactor 21 and strips $HCo(CO)_4$ (i.e., entrained volatile cobalt compounds) from the crude oxo product and carries it overhead in the vapor stream to an absorber (not shown). In the absorber, the $HCo(CO)_4$ is absorbed from the gas stream into a fresh olefin. The cobalt-loaded olefin is then used as feed to the oxo reactors.

Prior to delivering the entrained volatile cobalt compounds to the absorber, they are carried via conduit 23 to heat exchanger/condenser 89 which condenses out water, organics and dissolved cobalt carbonyls from the entrained gases of stripper reactor 21 at a temperature in the range between about 130°–160° C. and then passes the two phase mixture to reflux unit 28 wherein the gas phase is taken overhead via conduit 26 to an absorber (not shown) and the liquid phase is taken as bottoms. The liquid phase or reflux product may be recycled via conduit 22 to stripper reactor 21 or sent via conduit 24 to the preformer reactor (not shown), wherein it acts as a preformer reaction initiator in the conversion of cobalt formate to hydridocobalt tetracarbonyl. The reflux product recycled to reactor 21 via conduit 22 is injected at a point about stripper reactor 21 which is capable of forming a stripping zone in the upper portion of the stripper reactor and a reaction zone in the lower portion of the stripper reactor, i.e., intermediate stripper section 79. The two-phase liquid removed as bottoms from the stripper reactor via conduit 87 is preferably reduced in temperature by cooler 88 and thereafter separated by an oil-water separator (not shown). The aqueous phase typically includes water, dissolved cobalt formate (i.e., water soluble cobaltous salt), and formic acid. The organic phase typically includes aldehyde, dissolved water, and some formic acid. However, the constituent make-up of these phases will certainly differ depending upon the crude product feed injected into the stripper reactor.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A method for producing higher aldehydes and higher alcohols which comprises:

(a) hydroformylating an olefinic feedstock with synthesis gas in the presence of a cobalt-containing catalyst to form a crude product containing higher aldehyde, higher alcohol, secondary products and dissolved cobalt catalysts;

(b) contacting said crude product with an oxygen-containing gas, an organic acid and water, thereby producing a substantially cobalt-free organic hydroformylation reaction product and a water soluble cobaltous salt aqueous product;

(c) separating said substantially cobalt-free crude product from said water soluble cobaltous salt aqueous product;

(d) concentrating said water soluble cobaltous salt aqueous product, thereby producing a concentrated aqueous solution of cobaltous salt and a substantially cobalt-free aqueous solution;

(e) separating said concentrated aqueous solution of cobaltous salt from said substantially cobalt-free aqueous solution;

(f) contacting said concentrated aqueous solution of cobaltous salt with an alcohol and synthesis gas, and passing this mixture to a preformer reactor where said concentrated solution of cobaltous salt is converted to a cobalt carbonyl;

(g) passing said cobalt carbonyl to a stripping reactor wherein said cobalt carbonyl is contacted with a stream of stripping gas to entrain volatile cobalt compounds in said stripping gas; whereby said entrained volatile cobalt compounds are taken overhead; and (h) recycling at least a portion of said entrained volatile cobalt compounds taken overhead in step (g) to said preformer reactor.

2. The method according to claim 1 wherein said entrained volatile cobalt compounds include at least hydridocobalt tetracarbonyl which is capable of initiating the conversion of said concentrated aqueous solution of cobaltous salt to a cobalt carbonyl in step (f).

3. The method according to claim 1 wherein said concentrated aqueous solution of cobaltous salt is converted to a cobalt carbonyl in the presence of a noble metal catalyst disposed within said preformer reactor.

4. The method according to claim 3 wherein said noble metal catalyst is gold, platinum or palladium.

5. The method according to claim 1 wherein said preformer reactor is operated at a pressure in the range between about 103 bar to about 310 bar and a temperature in the range between about 100° C. to about 175° C.

6. The method according to claim 1 wherein said crude product of a cobalt-catalyzed hydroformylation reaction is prepared from olefins having carbon numbers in the range between about $C_4$ to about $C_{14}$.

7. The method according to claim 6 wherein said crude product of a cobalt-catalyzed hydroformylation reaction is prepared from olefins having carbon numbers in the range between about $C_5$ to about $C_7$.

8. The method according to claim 1 further comprising the steps of:

condensing said volatile cobalt compounds from step (g) to form a gaseous phase stream comprising gaseous cobalt carbonyl and a liquid phase stream comprising water, organics and dissolved cobalt carbonyl;

separating said gaseous phase stream from said liquid phase stream; and passing at least a portion of said liquid phase stream to said preformer reactor.

9. A method for producing higher aldehydes and higher alcohols which comprises:

(a) hydroformylating an olefinic feedstock with synthesis gas in the presence of a cobalt-containing catalyst to form a crude product containing higher aldehyde, higher alcohol, secondary products and dissolved cobalt catalysts;

(b) removing said cobalt catalysts from said crude product by contacting said crude product with water and an organic acid to form an aqueous crude product which is then contacted with a stream of stripping gas to entrain volatile cobalt compounds in said stripping gas; whereby said entrained volatile cobalt compounds are taken overhead and a substantially cobalt-free organic hydroformylation reaction product and a water soluble cobaltous salt are taken as bottoms;

(c) separating said substantially cobalt-free crude product from said water soluble cobaltous salt;

(d) contacting said water soluble cobaltous salt with an oxygen-containing gas, an organic acid and water, thereby producing a water soluble cobaltous salt aqueous product;

(e) concentrating said water soluble cobaltous salt aqueous product thereby producing a concentrated aqueous solution of cobaltous salt and a substantially cobalt-free water containing said organic acid;

(f) separating said concentrated aqueous solution of cobaltous salt from said substantially cobalt-free water containing said organic acid;

(g) contacting said concentrated aqueous solution of cobaltous salt with an alcohol and synthesis gas, and passing this mixture to a preformer reactor where said concentrated aqueous solution of cobaltous salt is converted to a cobalt carbonyl;

(h) passing said cobalt carbonyl from step (g) to step (b); and (i) passing at least a portion of said entrained volatile cobalt compounds taken overhead in step (b) to said preformer reactor.

10. The method according to claim 9 wherein said entrained volatile cobalt compounds include at least hydridocobalt tetracarbonyl which is capable of initiating the conversion of concentrated aqueous solution of cobaltous salt to a cobalt carbonyl in step (g).

11. The method according to claim 9 wherein said concentrated aqueous solution of cobaltous salt is converted to a cobalt carbonyl in the presence of a noble metal catalyst disposed within said preformer reactor.

12. The method according to claim 11 wherein said noble metal catalyst is gold, platinum or palladium.

13. The method according to claim 9 wherein said preformer reactor is operated at a pressure in the range between about 103 bar to about 310 bar and a temperature in the range between about 100° C. to about 175° C.

14. The method according to claim 9 wherein the crude product of a cobalt-catalyzed hydroformylation reaction is prepared from olefins having carbon numbers in the range between about $C_7$ to about $C_{20}$.

15. The method according to claim 14 wherein the crude product of a cobalt-catalyzed hydroformylation reaction is prepared from olefins having carbon numbers in the range between about $C_8$ to about $C_{14}$.

16. The method according to claim 9 further comprising the steps of:

condensing said volatile cobalt compounds from step (b) to form a gaseous phase stream comprising gaseous cobalt carbonyl and a liquid phase stream comprising water, organics and dissolved cobalt carbonyl;

separating said gaseous phase stream from said liquid phase stream; and passing at least a portion of said liquid phase stream to said preformer reactor.

17. A method for starting a preformer reactor disposed within a hydroformylation system which comprises an oxo reactor, a stripper reactor and a preformer reactor, wherein the bottoms from said stripper reactor comprise at least a water soluble cobaltous salt and wherein the overhead from said stripper reactor comprises entrained volatile cobalt compounds, the improvement characterized by the recycling of at least a portion of said entrained volatile cobalt compounds to said preformer reactor.

18. The method according to claim 17 wherein said entrained volatile cobalt compounds include at least hydridocobalt tetracarbonyl which is capable of initiating the conversion of said cobaltous salt to a cobalt carbonyl in said preformer reactor in the presence of synthesis gas.

19. The method according to claim 18 further comprising a noble metal catalyst disposed within said preformer reactor.

20. The method according to claim 19 wherein said noble metal catalyst is gold, platinum or palladium.

\* \* \* \* \*